United States Patent [19]

Curless et al.

[11] Patent Number: 4,461,950
[45] Date of Patent: Jul. 24, 1984

[54] HEATER FOR AIR BATH OVEN

[75] Inventors: Richard W. Curless, Westford; Robert L. Blanchard, Lexington, both of Mass.

[73] Assignee: The Foxboro Company, Foxboro, Mass.

[21] Appl. No.: 408,968

[22] Filed: Aug. 17, 1982

[51] Int. Cl.³ .......................... B01D 15/08; F24H 3/04
[52] U.S. Cl. .................................... 219/368; 219/364; 219/373; 219/374
[58] Field of Search ............... 219/367, 368, 376, 381, 219/280, 364, 494, 366, 374, 373, 379, 380, 382, 400; 73/23.01

[56] References Cited

U.S. PATENT DOCUMENTS

| | | | |
|---|---|---|---|
| 2,120,583 | 6/1938 | Timberlake | 219/373 |
| 2,396,190 | 3/1946 | Morgan et al. | 219/368 |
| 2,578,819 | 12/1951 | Mast et al. | 219/364 |
| 2,632,089 | 3/1953 | Buckmaster | 219/381 |
| 2,819,378 | 1/1958 | Nokes et al. | 219/368 |
| 2,849,589 | 8/1958 | Lancaster | 219/364 |
| 3,057,183 | 10/1962 | Ford | 219/280 |
| 3,111,023 | 11/1963 | Overfield | 219/280 |
| 3,310,652 | 3/1967 | Williams | 219/364 |
| 3,336,464 | 8/1967 | Hittenberger et al. | 219/373 |
| 3,778,223 | 12/1973 | Wheaton et al. | 219/373 |
| 3,823,306 | 7/1974 | Davis | 219/368 |
| 3,904,849 | 9/1975 | Lucero et al. | 219/368 |
| 4,147,923 | 4/1979 | Davis et al. | 219/368 |
| 4,286,140 | 8/1981 | Dewulf et al. | 219/368 |
| 4,336,442 | 6/1982 | Starr | 219/400 |

FOREIGN PATENT DOCUMENTS 1446417 8/1976 United Kingdom ................ 219/381
2009913A 6/1979 United Kingdom ................ 219/374

OTHER PUBLICATIONS

"Gas Heating System", by Wetz, in IBM Technical Disclosure Bulletin, vol. 21, No. 4, Sep. 1978.

Primary Examiner—Roy N. Envall, Jr.
Assistant Examiner—Geoffrey S. Evans
Attorney, Agent, or Firm—Jack H. Wu

[57] ABSTRACT

A heating device, usable in an oven for heating chromatographic equipment, includes an intake for passing an air flow produced by an air supply connected thereto into a cavity formed inside of a tubular member. A heating element, preferably located within that cavity, heats the air flow to an elevated temperature as well as the walls of the tubular member. A heater housing having an enclosed volume contains the tubular member. The heated air flow passes from the cavity into the enclosed volume where it is distributed along both the interior surfaces that define the enclosed volume and the outside of the walls of the tubular member. The interior surfaces are thereby heated while the heated air flow receives further heat from the heated cavity walls. A manifold including an elongated portion having a plurality of apertures formed therethrough with integral nozzles is connected to the heater housing for receiving therefrom the heated air flow. The elongated portion extends substantially parallel to the heater housing and is arranged such that the heated air flow leaving the nozzles is directed to impinge upon the warmed heater housing before it is circulated to heat the chromatographic equipment.

10 Claims, 3 Drawing Figures

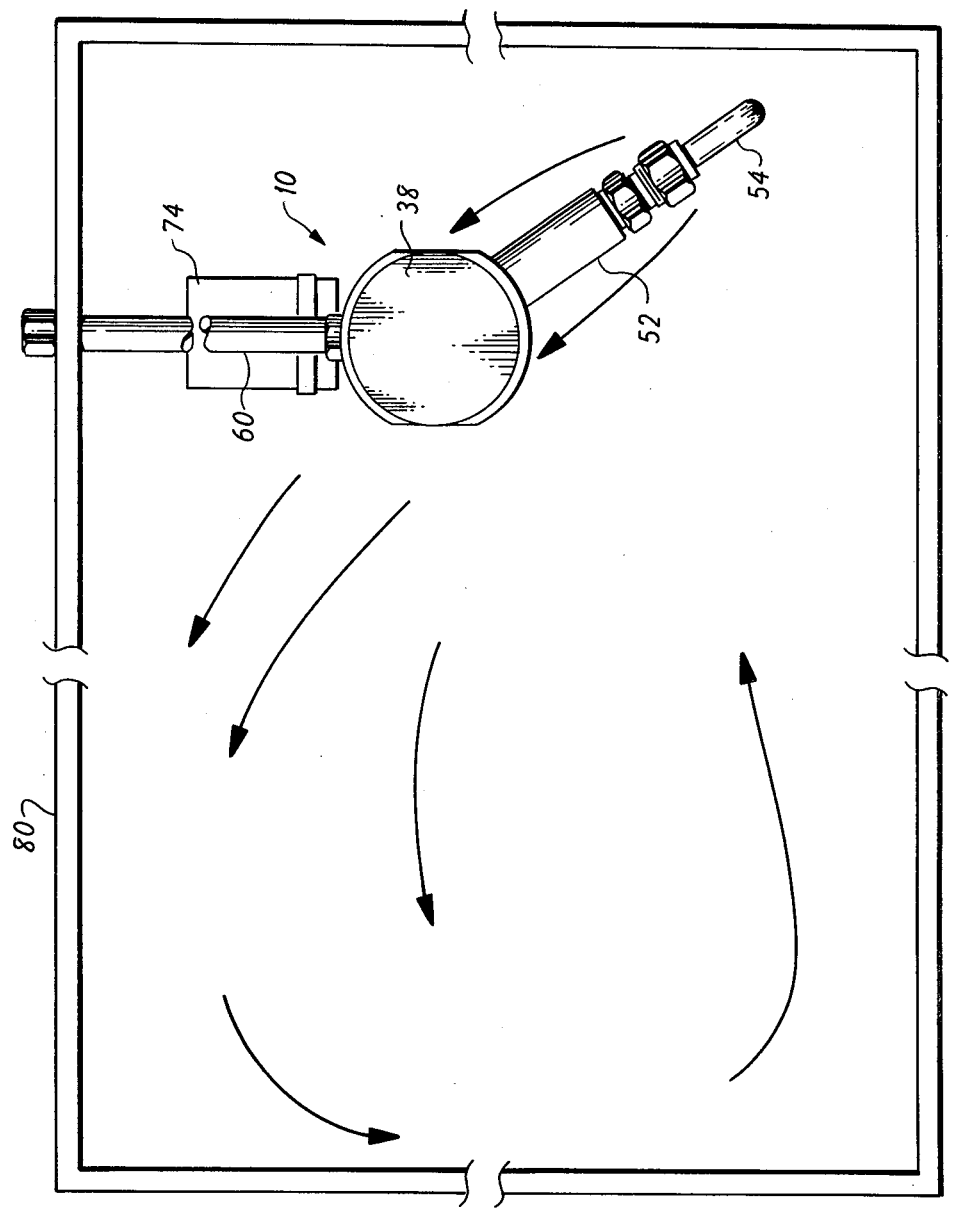

HEATER FOR AIR BATH OVEN

BACKGROUND OF THE INVENTION

The present invention relates to air bath ovens for heating chromatographic equipment, and more particularly, to heating apparatus for elevating the temperature of the air stream used to heat the equipment mounted inside the oven.

DESCRIPTION OF THE PRIOR ART

In elution-type chromatographic apparatus, a sample fluid is injected into a column which is used to separate components of that fluid so that measurements can be made by detectors. Various chromatographic equipment, particularly the detectors and the separation columns, are known to be temperature sensitive. Generally, these temperature-sensitive equipment are placed in a thermostatically controlled compartment arranged as an oven where temperature may be accurately maintained or varied in a programmed manner.

It is common to use an electrical heating element for elevating and maintaining the air temperature in the oven above ambient. Typically, the heating element is located inside the oven. However, in order to maintain the chromatographic equipment in the oven at a prescribed temperature, the heating element is operated at a temperature greater than the prescribed temperature. Accordingly, a local "hot spot" is produced in the oven and temperature gradients are thereby created which can adversely affect the temperature of the chromatographic equipment.

Various arrangements have been employed to overcome the problems caused by undesirable temperature gradients. In particular, a fan has been used to force the heated air in a controlled manner so that undesirable temperature gradients are virtually eliminated. Further, oven baffles have been used to partition the oven interior so that air circulation may be channeled and undesirable air flows are prevented.

While the above-described arrangements are satisfactory for their intended uses, they have a disadvantage in that the thermal mass of the oven is increased. This is particularly undesirable for temperature programmed ovens where such thermal mass may interfere with the rate at which the temperature is desired to be changed. Moreover, such arrangements undesirably increase the cost and complexities of such ovens. Therefore, there is a need for an improved heating device for use in chromatographic ovens.

SUMMARY

The above-mentioned disadvantages of prior art chromatographic devices are overcome by the provision of a new and improved heating apparatus made in accordance with the teachings of the present invention. In a preferred embodiment of the invention, a heater housing is formed with an enclosed volume having a longitudinal axis therethrough, a tubular member having a chamber therein is disposed within the enclosed volume, a heating means is mounted within the chamber, a manifold including an elongated portion extending parallel to the longitudinal axis is connected to the heater housing, and nozzles for directing a flow of heated air throughout the oven are coupled to apertures made in the elongated portion. An air supply connected to an inlet of the chamber produces an air flow into the tubular member. The air flow is heated by the heating means to a prescribed temperature greater than ambient. The chamber has an outlet for passing the heated air flow into the enclosed volume of the heater housing where it is directed over the interior surfaces defining the enclosed volume as well as over the outside of the tubular member. A conduit connecting the heater housing and the manifold carries the heated air flow into the elongated portion of the manifold. The heated air flow, after passing through the nozzles and impinging upon the exterior surfaces of the heater housing, is circulated throughout the rest of the oven for heating the chromatographic equipment located therein.

This arrangement of the present invention permits greater heat transfer between the heater element and the air flow than for prior art devices. Specifically, in addition to the conventional direct heating of the air flow by the heating element, heat is also transferred to the air flow when it is flowing over the outside of the tubular member and when it is flowing over the exterior surfaces of the heater housing. Increasing the sources of heat transfer allows the heater device of the present invention to be operated at a temperature close to that desired for heating the chromatographic equipment. Thus, temperature gradients in the oven are substantially reduced.

Moreover, if the air supply includes a source of pressurized air, the use of a fan is eliminated. Further, using nozzles to direct the heated air flow over the heater housing and over the interior of the oven eliminates the need for having oven baffles. Therefore, the present invention has the advantages attendant to its being relatively simple to construct and a design that reduces the thermal mass of a chromatographic oven.

The above-described and other features of the present invention will be more fully understood from a reading of the ensuing description given with reference to the appended drawings.

DESCRIPTION OF THE DRAWINGS

FIG. 3 depicts the present invention mounted inside a chromatographic oven enclosure.

DETAILED DESCRIPTION OF THE PREFERRED EMBODIMENT

Figure 1:
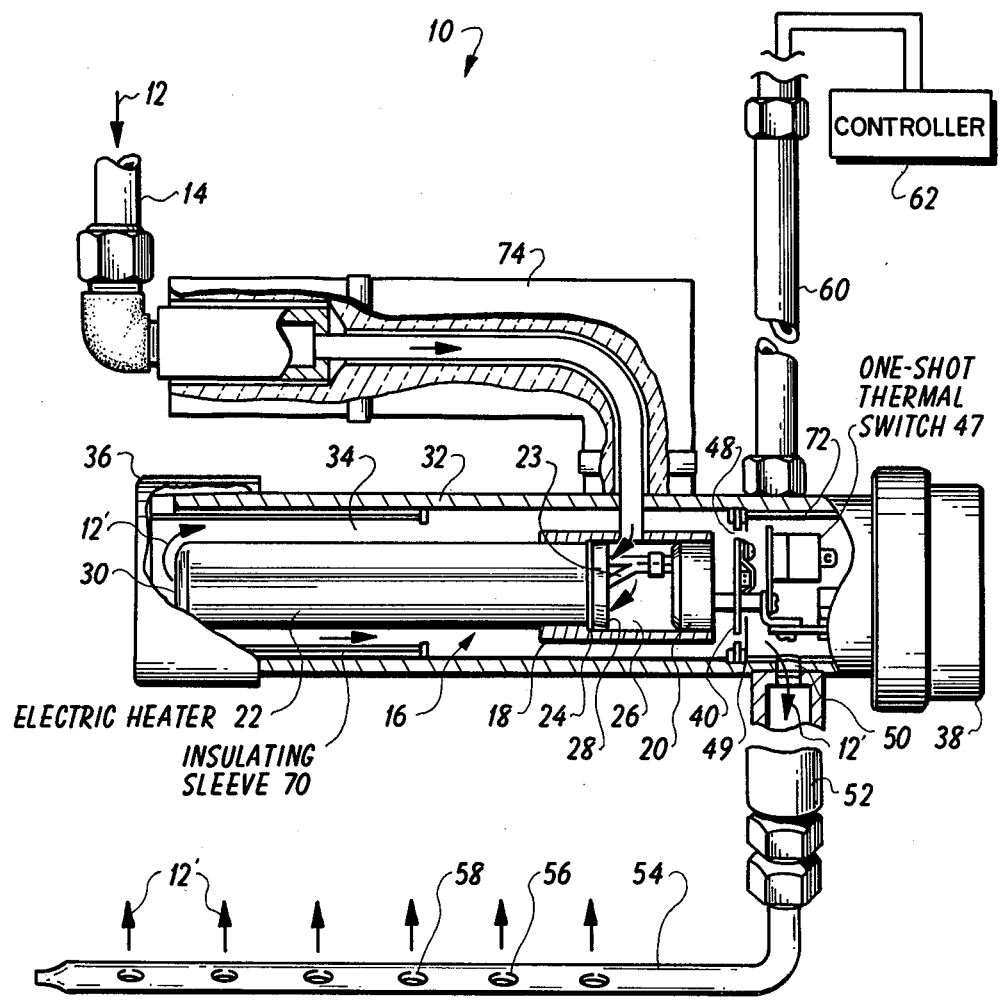
FIG. 1 is a partial sectional view of a heating apparatus made in accordance with the teachings of the present invention.

With reference to FIG. 1, a partial cutaway view of heating apparatus 10 for a chromatograph is depicted in which an air flow, represented by arrow 12, is applied to an intake pipe 14 and carried to heating cartridge 16. Cartridge 16 includes a cylindrically-formed member 18 which is sealed at one end by a plug 20, a heating core 22 which extends through and is mounted to the other end of member 18. Stop ring 24 serves to locate core 22 in member 18 and core 22. Cartridge 16 is thereby formed with an inlet cavity 26 for receiving air flow 12. Heating core 22 is a conventional heater formed with multiple tubes (not shown) which extend longitudinally from one end 28 to the other end 30 for carrying air flow 12 therethrough. Being a part of heating core 22, electrical heating elements mounted in the tubes operate to produce heated air flow 12'. Heater housing 32 is formed with a chamber 34 therein that is sealed at the front (left) end by insulated end cap 36 and sealed at the rear (right) end by threaded cap 38. Cap 38 is removed so that maintenance access can be gained to the interior of heater housing 32 as well as to heater cartridge 16.

Figure 2:
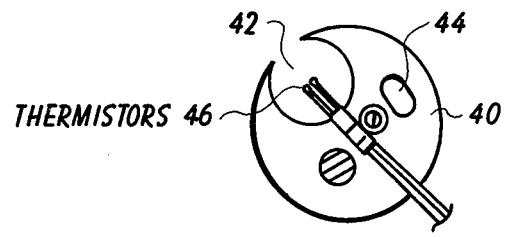
FIG. 2 is a frontal view of an element depicted in FIG. 1 with thermistors.

Located toward the rear portion of chamber 34 is baffle plate 40. A frontal view of plate 40 as seen from the right of FIG. 1 is depicted in FIG. 2. With the additional reference to that figure, openings 42 and 44 are formed in baffle plate 40 and arranged to pass heated air flow 12' therethrough. Dual thermistors 46 are mounted to extend into opening 42 and operate to sense the temperature of heated air flow 12' as it passes through baffle plate 40.

One-shot switch 47 is located opposite hole 42 so that heated air flow 12' will impinge the sensing surface thereof after that air flow has passed through hole 42 and past dual thermistors 46. The purposes of dual thermistors 46 and one-shot switch 47 will be explained in a later portion of this description. Small annular clearance 48 is formed around baffle 40 by rings 49 to permit easy assemblage of heating cartridge 16 in heater housing 32.

Outlet 50 formed at the bottom of the rear portion of chamber 34 is connected to conduit 52. Coupled to conduit 52 is manifold 54 having apertures 56 formed therethrough.

Although aperture size (diameter) is mostly dependent upon the amount of air flow desired to be passed therethrough, it has been discovered empirically that an aperture having a diameter equal to twice its depth acts like a nozzle for directing the heated air flow 12' from within the manifold to an outside location. Accordingly, surfaces 58 which define apertures 56 are also nozzles, integrally formed in manifold 54, so that no additional nozzle structure is required to be added to each aperture for controlling the direction of air flowing out of the manifold.

Electrical pipe 60 is coupled to heater housing 32 and provides a passageway by which electrical leads may be passed therethrough for connecting a controller 62 to heater core 22 (via leads 23) and dual thermistors 46. A description of controller 62 will be presented shortly in a later portion of this specification.

The operation of heating apparatus 10 will now be discussed. Air flow 12, preferably supplied under pressure ranging between 30-35 psi, enters chamber 26 and passes through heating core 22 for heating to an elevated temperature by the resistive elements located therein. Heated air flow 12' exits through end 30 of heating core 22 and enters chamber 34 where it is then applied to the inner surfaces of heater housing 32 as well as the outside of heating core 22. This arrangement permits heating core 22 to supply additional heat to heated air flow 12'.

One feature of the preferred embodiment of the present invention includes a limitation of the maximum temperature to which heated air flow 12' may be elevated. As further explanation, it should be recalled that dual thermistors 46 are positioned to sense the temperature of heated air flow 12' just before it is applied to conduit 52. It is desirable, especially in situations involving hazardous environments or gases, to limit the maximum temperature to which air flow 12 may be raised so as to prevent an explosion or a fire. Such condition is particularly critical during times of oven warmup or during open-door conditions. Accordingly, controller 62 includes electrical circuits that are well known in the art for cutting off the electrical power to heater core 22 when dual thermistors 46 sense a temperature equal to a prescribed maximum temperature. A dual thermistor design is preferred for the present invention because such design is more accurate than single thermistor arrangements for sensing the occurrence of the prescribed maximum temperature.

Inlet pipe 14 also includes conventional flame arrestor 63. A similar flame arrestor (not shown) is mounted inside conduit 52. These flame arrestors, well known in the art for safety, prevent any fires or explosions which may occur inside heater housing 32 from exiting back through inlet pipe 14 or forward through manifold 54.

Furthermore, being arranged as another safety feature of the present invention, one-shot switch 47 is set to open at a temperature slightly above the prescribed maximum temperature limit of the thermistors so that in the case of a failure in dual thermistors 46 or in the circuitry of controller 62, a provision still exists for shutting off the heater. In the preferred embodiment of applicant's invention, the one-shot switch 47 once activated to cut off the electrical current to heater core 22 must be manually reset before any further use of heater apparatus 10 is allowed. In its normal state, switch 47 is closed so that electrical power may be transmitted to heater core 22 when required.

With reference to FIG. 3, heating apparatus 10 is shown to be mounted in oven enclosure 80 which contains chromatographic equipment (e.g., columns). It can be seen that conduit 52 extends at an angle down from heater housing 32 and that heated air flow 12' upon exiting manifold 54 through nozzles 58. Thereafter, the heated air flow entrains surrounds oven air and impinges upon the outer surfaces of heater housing 32. Since heater housing 32 has been previously warmed, additional heat is provided to heated air flow 12' and the entrained oven air before they are circulated throughout the remaining interior of oven 80. Thus, since heat transfers to air flow 12 occur in three regions of heater apparatus 10, the overall temperature of that apparatus may be maintained closer to the prescribed temperature desired for the oven interior so that hot spots and attendant undesirable temperature gradients are substantially minimized. It should be noted that angling conduit 52 permits greater use of the oven interior than if it descended parallel to the side wall of oven 80 and, also, induces rotary circulation in the oven interior.

A conventional thermostat (not shown) is positioned within the oven interior for measuring the air temperature therein. That thermostat and associated circuitry are well known in the art, and explanation of such is not needed for the understanding of the present invention. However, it should be understood that controller 62 operates in conjunction with the conventional thermostat and associated circuitry in order that heater apparatus 10 is on for the periods necessary to elevate and maintain the oven interior at a prescribed temperature.

With reference back to FIG. 1, a further design feature of the present invention involves the insulation added to heating apparatus 10. End cap 36 is lined with an insulative material and the front portion of the interior surface of heater housing 32 is covered by sleeve 70 which is also made of an insulative material. This arrangement prevents hot spots from forming on the front portions of heater housing 32 where heated air flow 12' inside chamber 34 initially leaves heating core 22. In other words, this arrangement permits even heating of heater housing 32 so that uniform heat transfer is provided to the air flow leaving manifold 54 and impinging on the housing 32. In addition, the rear portion of the interior surface defining chamber 34 is covered by an electrically insulative sleeve 72 for isolating electrical terminals (which may be located therein) from contacting the heater housing 32.

Finally, input pipe 14 further includes an insulative jacket 74. Since input air flow 12 is cooler than heated air flow 12′, it is desirable to isolate that input air flow and pipe 14 so that they will not remove heat from any portions of heated air flow 12′ (leaving manifold 54) which may contact this part of the present invention.

While the present invention has been described with reference to several embodiments, it will be apparent that improvements and modifications may be made within the purview of the invention without departing from the true spirit and scope thereof as defined in the appended claims.

We claim:

1. An apparatus for heating chromatographic equipment disposed within an oven enclosure, said apparatus comprising:
    air supply means for generating an air flow having a pressure greater than ambient and thereby resulting in said air flow being forced through said apparatus;
    a housing including interior and exterior surfaces which form an enclosed volume that has a longitudinal axis extended therethrough;
    first conduit means for connecting said air supply means to said housing and for passing said air flow into said enclosed volume;
    heating means including an outside area, an inlet, an outlet and an interior heating element, said heating means being disposed in said enclosed volume and coupled to said first conduit means so that said air flow is heated by flowing through said interior heating element and applied to said outlet;
    flow directing means adjacent said outlet for deflecting said heated air flow along both said outside area of the heating means and said interior surface of the enclosed volume;
    a manifold being external of said housing and including an elongated portion disposed parallel to said longitudinal axis;
    second conduit means for connecting said manifold to said enclosed volume of the housing and for passing said deflected heated air flow into said elongated portion; and
    said elongated portion including an opening which is opposite said housing so that said deflected heated air flow passes therethrough for impinging on said exterior surface of the housing.

2. The apparatus of claim 1, further including a one-shot switch coupled to said heating means and arranged to open and thereby stop operation of said heating means whenever the temperature of said deflected heated air flow exceeds a predetermined temperature, said one-shot switch remaining open even after the temperature of the deflected heated air flow subsequently becomes less than said predetermined temperature.

3. The apparatus of claim 1, further comprising a control circuit which includes at least one temperature sensor for sensing the temperature of said deflected heated air flow, said control circuit operable to stop operation of said heating means whenever the temperature sensed by the temperature sensor equals a predetermined temperature and to restore subsequent operation of said heating means whenever the sensed temperature of the deflected heated air flow becomes less than said predetermined temperature.

4. The apparatus of claim 1 wherein said elongated portion further includes a nozzle formed around said opening for directing said deflected heated air flow and entraining ambient air surrounding said nozzle to impinge on the exterior surface of the housing.

5. The apparatus of claim 4 wherein said first conduit means further includes a duct which extends into said enclosed volume of the housing and through which said air flow passes, said duct being connected to said heating means and disposed in said enclosed volume so that said deflected heated air flow passes around the outside of said duct.

6. The apparatus of claim 5 wherein said housing further includes an end cap, the interior portion of which being insulated and forming part of said interior surface of the housing, and said insulated interior portion being disposed opposite said outlet of the heating means.

7. The apparatus of claim 6 wherein part of said interior surface is insulated for a prescribed portion which extends from a section proximate said heating means outlet and along said enclosed volume.

8. The apparatus of claim 7 further comprising a control circuit which includes at least one temperature sensor for sensing the temperature of said deflected heated air flow, said control circuit operable to stop operation of said heating means whenever said temperature equals a predetermined temperature and to restore subsequent operation of said heating means whenever the sensed temperature of the deflected heated air flow becomes less than said predetermined temperature.

9. The apparatus of claim 7 further comprising a one-shot switch coupled to said heating means and arranged to open and thereby stop operation of said heating means whenever the temperature of said deflected heated air flow exceeds said predetermined temperature, said one-shot switch remaining open even after the sensed temperature of the deflected heated air flow subsequently becomes less than said predetermined temperature.

10. The apparatus of claim 1 wherein said first conduit means further includes a duct which extends into said enclosed volume of the housing and through which said air flow passes, and said duct being connected to said heating means and disposed in said enclosed volume so that said deflected heated air flow passes around the outside of said duct.

* * * * *